US009301965B2

(12) United States Patent
Acevedo-Duncan et al.

(10) Patent No.: US 9,301,965 B2
(45) Date of Patent: Apr. 5, 2016

(54) METHOD OF TREATING OVARIAN CANCER USING A PKC INHIBITOR

(71) Applicants: Mildred Enid Acevedo-Duncan, Plant City, FL (US); David Ostrov, Gainesville, FL (US); Minjel Shah, Bloomfield Hills, MI (US); Christopher Apostolatos, Tampa, FL (US); Hercules Apostolatos, Brandon, FL (US)

(72) Inventors: Mildred Enid Acevedo-Duncan, Plant City, FL (US); David Ostrov, Gainesville, FL (US); Minjel Shah, Bloomfield Hills, MI (US); Christopher Apostolatos, Tampa, FL (US); Hercules Apostolatos, Brandon, FL (US)

(73) Assignees: University of South Florida, Tampa, FL (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/745,028

(22) Filed: Jun. 19, 2015

(65) Prior Publication Data

US 2015/0366883 A1    Dec. 24, 2015

Related U.S. Application Data

(60) Provisional application No. 62/014,176, filed on Jun. 19, 2014.

(51) Int. Cl.
| | |
|---|---|
| *A61K 31/664* | (2006.01) |
| *A61K 31/166* | (2006.01) |
| *A61K 31/4164* | (2006.01) |
| *A61K 31/675* | (2006.01) |
| *A61K 31/122* | (2006.01) |

(52) U.S. Cl.
CPC ............. *A61K 31/675* (2013.01); *A61K 31/122* (2013.01); *A61K 31/664* (2013.01); *A61K 31/166* (2013.01); *A61K 31/4164* (2013.01)

(58) Field of Classification Search
CPC    A61K 31/664; A61K 31/166; A61K 31/4164
See application file for complete search history.

(56) References Cited

U.S. PATENT DOCUMENTS

| | | | |
|---|---|---|---|
| 5,583,242 A | 12/1996 | Schieven | |
| 2009/0311681 A1 | 12/2009 | Faure | |
| 2012/0283194 A1* | 11/2012 | Atwood | .................... C07K 7/06 514/19.5 |
| 2013/0189257 A1 | 7/2013 | Acevedo-Duncan et al. | |

FOREIGN PATENT DOCUMENTS

WO    WO 2009126335 A2 *  10/2009    ........... A61K 31/122

OTHER PUBLICATIONS

Couldwell WT, Antel JP, Apuzzo ML, Yong VW. Inhibition of growth of established human glioma cell lines by modulators of the protein kinase-C system. J Neurosurg 1990;73:594-600.
Okhrimenko H, Lu W, Xiang C, Hamburger N, Kazimirsky G, Brodie C. Protein Kinase C-ε Regulates the Apoptosis and Survival of Glioma Cells. Cancer Res 2005;65:7301-7309.
Stensman H, Larsson C. Protein kinase C epsilon is important for migration of neuroblastoma cells. BMC Cancer 2008;8:365.
Nishizuka, Y., Intracellular signaling by hydrolysis of phospholipids and activation of protein kinase C. Science, Oct. 23, 1992. vol. 258, No. 5082, pp. 607-614.
Hirai, T. et al. PKC Zeta II, a small molecule of protein kinase C zeta, specifically, expressed in the mouse brain. 2003 Neuroscience Lett. 348, 151-154.
Hayashi, A.et al., PKCnu, a new member of the protein kinase C family, composes a fourth subfamily with PCKmu. Biochim. et Biophys. Acta. 1999; 1450, 99-106.
Fields AP, Regala RP. Protein kinase C iota: Human oncogene, prognostic marker and therapeutic target. Pharmacol Res 2007; 55:487-97.
Eder, A. et al., Atypical PKC-$\iota$ contributes to poor prognosis through loss of apical-basal polarity and Cyclin E overexpression in ovarian cancer, PNAS, 2005, 102(35):12519-12524.
Hirai T. et al., Protein Kinase Czeta (PKCzeta): activation mechanisms and cellular functions, J. Biochem., (2003), 133 (1):1-7.
Nazarenko I., et al., Atypical Protein Kinase C Zeta Exhibits a Proapoptotic Function in Ovarian Cancer, Molecular Cancer Research, 2010, 8(6):919-34.
Seto, K., et al., Atypical Protein Kinase C Zeta: Potential Player in Cell Survival and Cell Migration of Ovarian Cancer, PLoS One, 2015, 10(4):e123528.
Roffey, J. and Ott, G. Section editors, Modulators of Atypical Protein Kinase C as Anticancer Agents in Annual Reports in Medicinal Chemistry, Desai, M. editor, Academic Press, 2014, vol. 49:189-202.
Sajan, P., et al. Uncoupling Akt and FoxO1 by aPKC in Obesity. Diabetes. Apr. 4, 2014. pp. 1-28.
Pillai, P., et al. A novel PKC-$\iota$ inhibitor abrogates cell proliferation and induces apoptosis in neuroblastoma. The Inter. J. Biochem. & Cell Biol. 43:784-794(2011).
Rosse, C, et al (2014) Control of MT1-MMP transport by atypical PKC during breast-cancer progression. Proc Natl Acad Sci USA, 111(18):E1872-9.
Chen, Q. et al., Hedgehog signaling pathway and ovarian cancer, Chinese Journal of Cancer Research, 2013, 25 (3):346-53.
Umemori, Y et al (2014) PKC-$\zeta$ regulates survivin expression and inhibits apoptosis in colon cancer. Intl J Oncol. 2014, 45:1043-1050.
Atwood, SX et al (2014) "Atypical" regulation of Hedgehog-dependent cancers. Cancer Cell, 25(2):133-4.
International Search Report for PCT Application No. PCT/US15/36764, Interntional Filing date Jun. 19, 2015.

* cited by examiner

*Primary Examiner* — Samira Jean-Louis
(74) *Attorney, Agent, or Firm* — Michele L. Lawson; Smith & Hopen, P.A.

(57) ABSTRACT

A method of treating ovarian cancer by administering a PKC inhibitor is presented herein. It was found that administering a PKC inhibitor, such as ACPD or ICA-1, to ovarian cancer cells inhibited cancer cell proliferation.

12 Claims, 6 Drawing Sheets

METHOD OF TREATING OVARIAN CANCER USING A PKC INHIBITOR

CROSS REFERENCE TO RELATED APPLICATIONS

This application is a nonprovisional of and claims priority to U.S. Provisional Patent Application No. 62/014,176, entitled "Method of Treating Ovarian Cancer Using a PKC Inhibitor", filed Jun. 19, 2014, the entire contents of which is herein incorporated into this disclosure.

FIELD OF INVENTION

This invention relates to treating ovarian cancer. Specifically, the invention describes methods of treating ovarian cancer using a PKC inhibitor such as 2-acetyl-1,3-cyclopentanedione (ACPD) or ICA-1.

BACKGROUND OF THE INVENTION

Ovarian cancers are highly lethal tumors which account for approximately four percent of all women's cancers and are the fifth leading cause of cancer-related death among women.

Ovarian cancer is defined as cancer that forms in the tissues of the ovary (National Cancer Institute. (n.d.) *Ovarian Cancer*). Most ovarian cancers start in either the cells on the surface of the ovary (epithelial carcinoma) or in the egg cells themselves (germ cell tumors) (National Cancer Institute. (n.d.) *Ovarian Cancer*). According to the Centers for Disease Control and Prevention, ovarian cancer is responsible for more deaths among women than any other cancer of the reproductive system (Centers for Disease Control and Prevention. (2014, March) *Ovarian Cancer*). There have been 14,270 cases of ovarian cancer in 2014 alone (National Cancer Institute. (n.d.) *Ovarian Cancer*). One of every 68 women will develop ovarian cancer in their lifetime (Tung, C H et al (2014) Lessons learned from imaging mouse ovarian tumors: the route of probe injection makes a difference. Quant Imaging Med Surg, 4(3):156-162). Early diagnosis of ovarian cancer increases the chances of survival but only 14.7% of ovarian cancers are diagnosed in the local stage where the cancer has not spread outside the ovary (National Cancer Institute. (n.d.) *Cancer Statistics*).

The difficulty in catching ovarian cancers early lies in the fact that there may be no symptoms or the symptoms may be very common such as bloating and abdominal pain. Women with a family history of ovarian cancer or between the ages of 55 and 64 are most frequently diagnosed with ovarian cancer (National Cancer Institute. (n.d.) *Cancer Statistics*). Treatments for ovarian cancer include cytoreductive surgery and chemotherapy (Khabele, D (2014) The Therapeutic Potential of Class I Selective Histone Deacetylase Inhibitors in Ovarian Cancer. Front Oncol, 4; 4: 111). Cytoreductive surgery aims to debulk the tumor while platinum-based chemotherapy serves as a systemic therapy. Despite the treatment options available, women with advanced stages of ovarian cancer have low chances of survival.

Ovarian cancer patients often initially respond well to the platinum-based chemotherapy but eventually experience lower survival outcomes due to chemotherapy-induced resistance which can often occur rapidly and become fatal (Echevarría-Vargas I M, et al (2014) Upregulation of miR-21 in Cisplatin Resistant Ovarian Cancer via JNK-1/c-Jun Pathway. PLoS ONE 9 (5)).

At diagnosis the majority of patients have metastatic disease and the long-term survival remains low. Certain ovarian cancers are highly lethal tumors due to the emergence of therapy-resistant ovarian cancer cells.

Protein Kinase C (PKC) and Ovarian Cancer

The protein kinase C (PKC) family of Ser/Thr kinases is involved in transmembrane signal transduction pathways triggered by various extra and intracellular stimuli (Nelson D L Cox M M. Biosignaling. Lehninger Principles of Biochemistry. 3rd ed. New York: Worth Publishers; 2001. p. 469). They are involved in the control of cellular responses that include proliferation, migration, apoptosis and survival (Couldwell W T, Antel J P, Apuzzo M L, Yong V W. Inhibition of growth of established human glioma cell lines by modulators of the protein kinase-C system. J Neurosurg 1990; 73:594-0; Okhrimenko H, Lu W, Xiang C, Hamburger N, Kazimirsky G, Brodie C. Protein Kinase C-ε Regulates the Apoptosis and Survival of Glioma Cells. Cancer Res 2005; 65:7301-7309; Stensman H, Larsson C. Protein kinase C epsilon is important for migration of neuroblastoma cells. BMC Cancer 2008; 8:365). PKC regulates cellular functions, metabolism and proliferation by phosphorylating proteins in response to transmembrane signals from hormones, growth factors, neuro-transmitters and pharmacological agents.

Protein kinase C (PKC) is a family of fourteen known isozymes found in varying ratios in the cytosolic and membrane fractions of cells, depending on the type of tissue and its physiological state (Nishizuka 1992 *Science* 258, 607). PKC isozymes can be classified into three groups. Group I includes $Ca^{2+}$ dependent isozymes: cPKC-alpha, cPKC-betaI cPKC-betaII and cPKC-gamma. Isozymes in group II, nPKC-epsilon, nPKC-delta, nPKC-eta and nPKC-theta are $Ca^{2+}$ independent. Group III includes the atypical PKC: aPKC-iota (Selbie et al. 1993 *J. Biol. Chem.* 268, 24296), aPKC-zeta, aPKC-zetaII (Hirai et al. 2003 *Neuroscience Lett.* 348, 151), aPKC-mu (protein kinase D) and aPKC-nu (Hayashi et al. 1999 *Biochim. et Biophys. Acta.* 1450, 99) which are insensitive to both diacylglycerol and calcium and neither bind to nor are activated by phorbol esters. PKC-ζ and PKC-ι exhibit 72% sequence homology at the amino acid level. This structural similarity coupled with the fact that many commercial immunological reagents do not distinguish between these isoforms, has made it difficult to biochemically distinguish between PKC-ζ and PKC-ι. (Fields A P, Regala R P. Protein kinase Cι: Human oncogene, prognostic marker and therapeutic target. Pharmacol Res 2007; 55:487-97)

Protein kinase C-iota (PKC-ι) has been shown to aid in the ability of cancer cells to resist drug-induced apoptosis. Recently, it has been reported that PKC-ι which is located in chromosome 3 at 3q26.2 is the most common genomic amplicon as identified by comparative genomic hybridization (Eder A M, Sui X, Rosen D G, Nolden L K, Cheng K W, Lahad J P, Kango-Singh M, Lu K H, Warneke C L, Atkinson E N, Bedrosian I, Keyomarsi K, Kuo W L, Gray J W, Yin J C, Liu J, Halder G, Mills G B. Atypical PKC iota contributes to poor prognosis through loss of apical-basal polarity and cyclin E overexpression in ovarian cancer. *Proc Natl Acad Sci USA* 102:12519-12524 (2005)).

PKC-ι protein is markedly increased or mislocalized in all serous ovarian cancers. In nonserous ovarian cancers, increased PKC-ι protein levels, particularly in the presence of Cyclin E, are associated with markedly decreased overall survival. Additionally, an increase in PKC-ι DNA copy number was associated with decreased progression-free survival of ovarian cancer patients. (Eder, A. et al., Atypical PKC-ι contributes to poor prognosis through loss of apical-basal polarity and Cyclin E overexpression in ovarian cancer, PNAS, 2005, 102(35):12519-12524). Moreover, only PKC-ι gene amplification is highly correlated with protein overexpression, tumor size, lymph node metastasis and clinical stage out of four genes studied on the 3q26 amplification [*Genes Chromosomes Cancer* 47:127-136 (2008)].

Like other PKC isoforms, protein kinase-C zeta (PKC-ζ) is a serine/threonine kinase that adds phosphate groups to target proteins. It is atypical in that unlike other PKC isoforms, PKC-ζ does not require calcium or diacylglycerol (DAG) to become active, but rather relies on a different second messenger, presumably generated through a phosphoinositide 3-kinase (PI3-kinase) pathway. Protein kinase-C zeta (PKC-ζ) has been widely implicated in the regulation of cellular functions such as being a key regulator of critical intracellular signaling pathways induced by various extracellular stimuli. Studies have demonstrated the involvement of PKC-ζ in the mitogen-activated protein kinase cascade, transcriptional factor NFkB activation, ribosomal S6-protein kinase signaling, and cell polarity. An important molecular event in a cell is the association of PKC-ζ with other signaling molecules, as well as scaffold proteins, to form large complexes that regulate their pathways. (Hirai T. et al., Protein Kinase Czeta (PKC-zeta): activation mechanisms and cellular functions, *J. Biochem.*, (2003), 133(1):1-7).

PKC-ζ has been shown to be upregulated in ovarian carcinomas. It was found that expression of PKC-ζ in normal surface ovarian epithelial cells and in cystadenomas is absent or very low. However, most human ovarian adenocarcinomas expressed high amounts of PKC-ζ, which correlated with poor prognosis. (Nazarenko I., et al., Atypical Protein Kinase C Zeta Exhibits a Proapoptotic Function in Ovarian Cancer, *Molecular Cancer Research*, 2010, 8 (6):919-34) Recent studies have supported that PKC-ζ is a potential regulatory component of the IGF1R and ITGB3 pathways and may have a critical role in ovarian tumorgenesis. Researchers found that up-regulation of PKC-ζ leads to expression alterations of IGF1R and ITGB3 in SKOV3 and OVCAR3 cell lines, suggesting that PKC-ζ may participate in ovarian cancer progression by modulating the expression of other important signaling molecules. Further, an increase in cell proliferation in SKOV3 cells was shown when PKC-ζ was over-expressed and SKOV3 cells exhibited a decrease in cell migration when endogenous PKC-ζ expression was down-regulated by small-interference RNA (siRNA). (Seto, K., et al., Atypical Protein Kinase C Zeta: Potential Player in Cell Survival and Cell Migration of Ovarian Cancer, *PLoS One*, 2015, 10(4):e) 123528).

PKC Inhibitors

PKC inhibitors range in their selectivity for a particular class of PKCs. It has been suggested that only atypical isoforms of the PKC family contain the PB 1 domain and thus agents that disrupt signaling through this mechanism should be specific for atypical PKCs. Sodium aurothiomalate (ATM) (1) and aurothioglucose (ATG) (2) both seem to bind in the low micromolar range to PKC-ι, and as such, may be alternatives for PKC-ι specific inhibitors. Another gold-containing drug, auranofin (3), has a similar structure and thus may also have potential as a PKC inhibitor. Structures for the gold-containing inhibitors are shown below. (Roffey, J. and Ott, G. Section editors, Modulators of Atypical Protein Kinase C as Anticancer Agents in *Annual Reports in Medicinal Chemistry*, Desai, M. editor, Academic Press, 2014, Vol. 49:189-202)

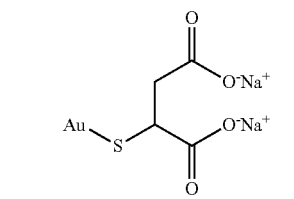

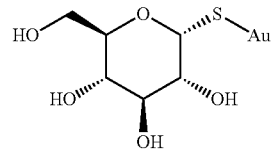

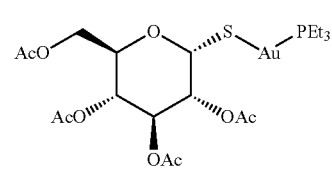

PKC-iota inhibitor [4-(5-amino-4-carbamoylimidazol-1-yl)-2,3-dihydroxycyclopentyl]methyl dihydrogen phosphate, known as (ICA-1) (4), is a small molecule inhibitor which binds to the catalytic domain of human PKC-ι, at amino acid residues 469-475 (glutamine-469, isoleucine-470, arginine-471, isoleucine-472, proline-473, arginine-474, serine-475). ICA-1 is an inhibitory agent specific to PKC-ι. Structure of PKC-ι is shown below.

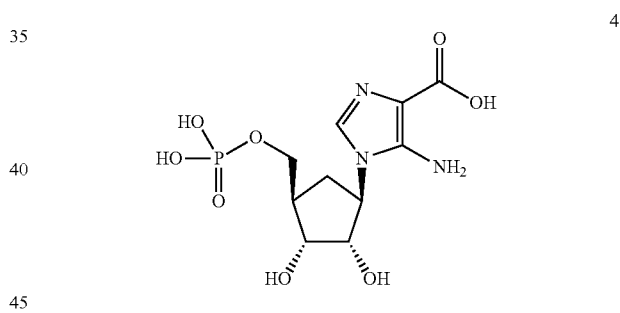

2-acetyl-1,3-cyclopentanedione (ACPD) is a pan-aPKC inhibitor which inhibits both PKC-ζ and PKC-ι, but not PKC-α, PKC-β, PKC-δ, or PKC-ε. The structure of ACPD is shown below:

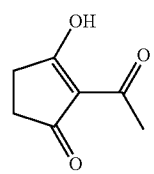

Pachastrissamine and its stereoisomers (6-10) have demonstrated cytotoxic effects on several cancer cell lines with potencies in the submicromolar range. Complete inhibition of both PKC-ζ and PKC-ι at 10 μM has been observed with only modest effects for novel and classical PKC isoforms. Screening at lower concentrations showed about 50% inhibition at 3 μM and no inhibition at 1 μM. Structures for pachastrissamine and its stereoisomers are shown below. (Roffey 2014)

A series of speciosterosulfates (sterolsulfates) (20-23), isolated from the marine sponge *Spheciospongia*, have been found to inhibit PKC-ζ. Structures for speciosterosulfates are shown below. (Roffey 2014)

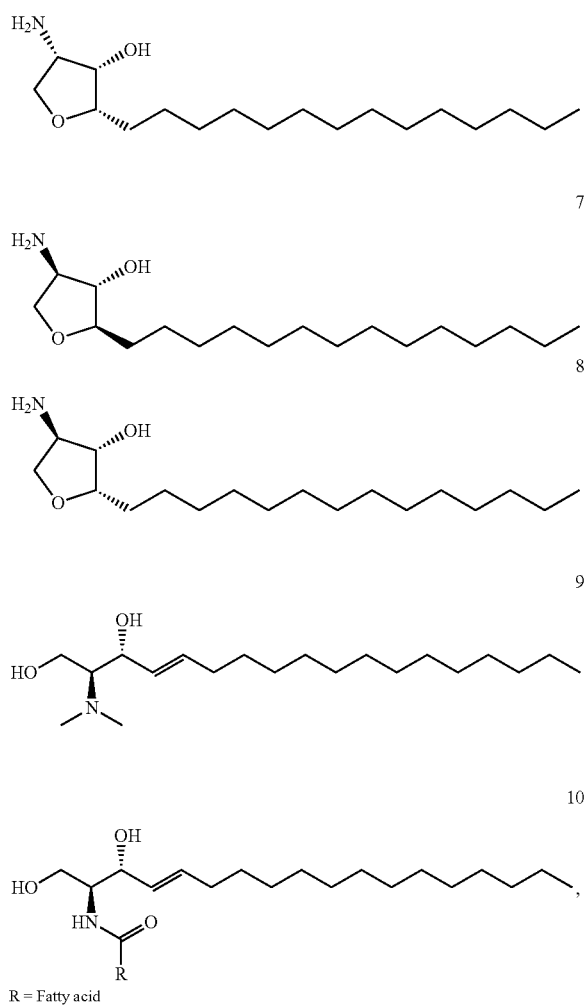

Several allosteric inhibitors (12-14) which bind the PIF-1 site and regulate activity through the C1 domain as well as a series of phenylthiopenes (15-17) may also have implications as potential aPKC inhibitors. Structures for the allosteric inhibitors (12-14) and the phenylthiopenes (15-17) are shown below. (Roffey 2014)

A 13-mer PKC-ζ inhibitory peptide (ZIP) (11) is myristoylated at the N-terminus to improve cell penetration and may serve as a novel PKC-ζ specific therapeutic. Structure of ZIP is shown below. (Roffey 2014)

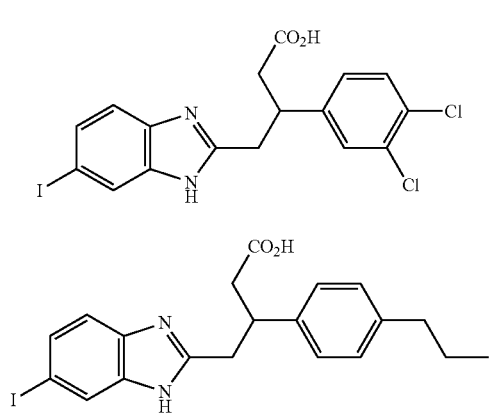

13

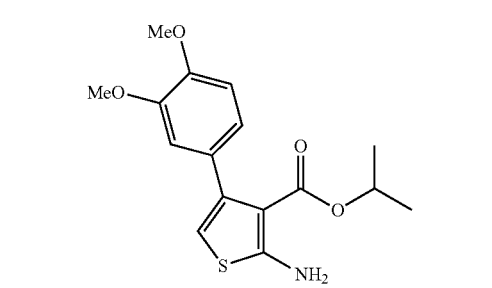

14

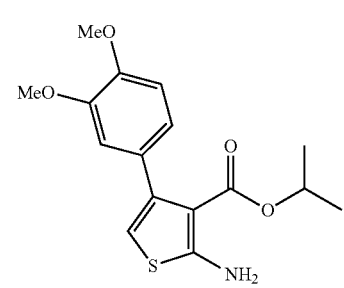

15

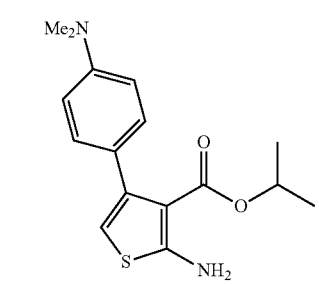

16

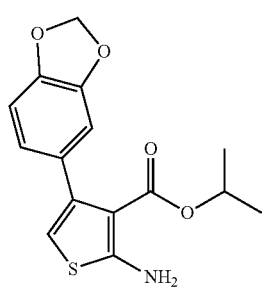

17

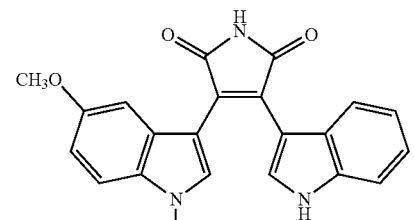

19

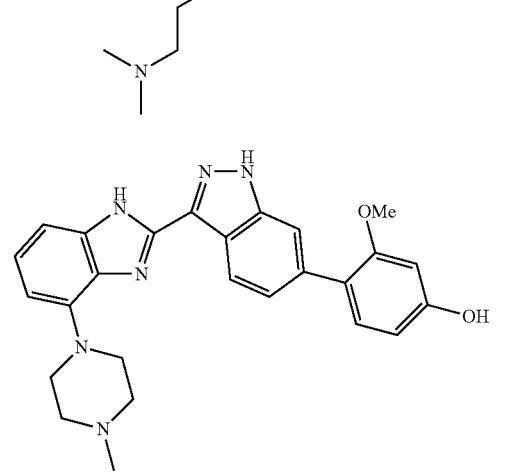

24

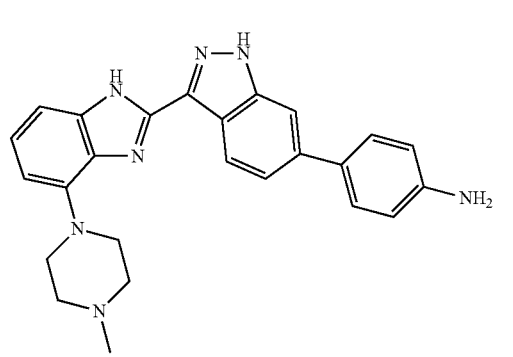

25

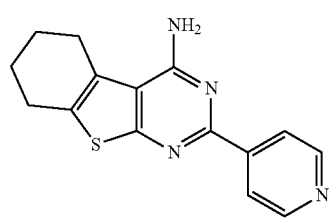

26

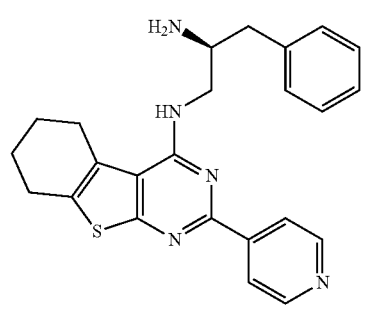

27

Other potential PKC inhibitors include, but are not limited to: a compound containing a maleimide substructure (19); a series of compounds having an indazole-benzimidazole motif (24-25); a series of ATP-competitive thieno[2,3-d]pyrimidine analogues (26-27); a pyrrole amide PKCzI257.3 (28); and a series of 3-hydroxy-2-(3-hydroxyphenyl)-4H-1-benzopyran-4-ones which may bind to the ATP-cleft of the kinase through a keto-hydroxyl motif in multiple conformations (30-33). Structures for the above listed potential PKC inhibitors are shown below. (Roffey 2014)

-continued

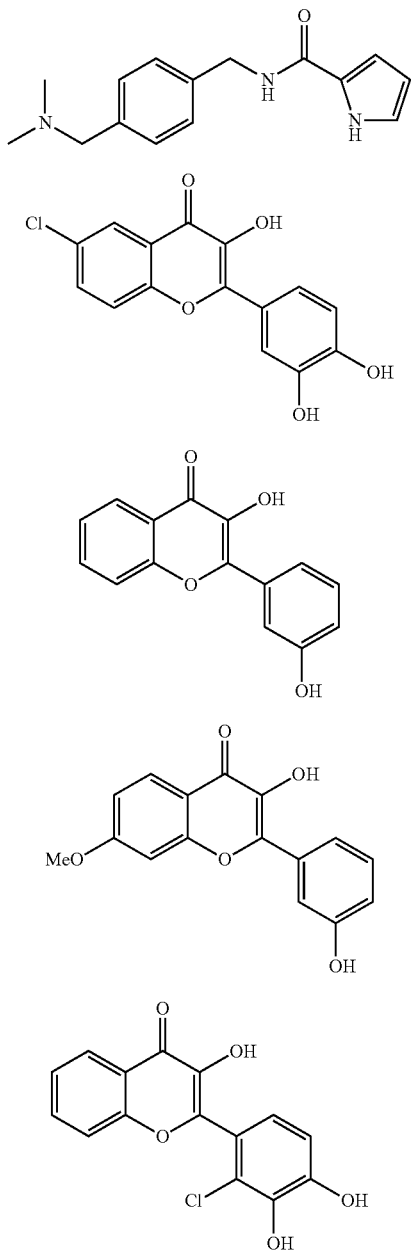

In light of the current difficulties in ovarian cancer treatment, particularly the emergence of therapy-resistant ovarian cancer cells, what is needed is a new method of treating ovarian cancer which overcomes the obstacles of the prior art.

SUMMARY OF INVENTION

Ovarian cancers are highly lethal tumors which account for approximately four percent of all women's cancers and are the fifth leading cause of cancer-related death among women. At diagnosis the majority of patients have metastatic disease and the long-term survival remains low. Certain ovarian cancers are highly lethal tumors due to the emergence of therapy-resistant ovarian cancer cells. The inventors have developed a novel method of treating ovarian cancer focusing on inhibiting atypical PKCs such as PKC-ζ and PKC-ι.

The inventors have determined the in-vitro efficacy of the pan-atypical protein kinase C (PKC) inhibitor, 2-acetyl-1,3-cyclopentanedione (ACPD) and the novel PKC-iota inhibitor, ICA-1, ([4-(5-amino-4-carbamoylimidazol-1-yl)-2,3-dihydroxycyclopentyl]methyl dihydrogen phosphate) on HEY ovarian cancer cell proliferation and RNA concentration. It was found that ACPD inhibits both PKC-iota (PKC-ι) and PKC-zeta (PKC-ζ) while ICA-1 inhibits only PKC-iota (PKC-ι).

Results showed that incubation of HEY ovarian cancer cells with ICA-1 or ACPD decreased proliferation and reduced RNA levels which suggest the potential of ACPD and ICA-1 as chemotherapeutic agents. ACPD may be used as a chemotherapeutic agent for ovarian cancer patients that have PKC-ι or PKC-ζ overexpression in their tumors while ICA-1 may be used as a chemotherapeutic agent for those patients whose tumors overexpress PKC-ι.

A method of treating ovarian cancer in a patient in need thereof is presented comprising administering a therapeutically effective amount of a protein kinase C (PKC) inhibitor. The PKC inhibitor may inhibit at least one atypical protein kinase (aPKC) selected from the group consisting of PKC-ι, PKC-ζ, or combinations thereof. In some embodiments, the PKC inhibitor is specific to a single aPKC while in other embodiments the PKC inhibitor is a pan-aPKC inhibitor which is effective against different isoforms of aPKC. An example of a PKC-specific inhibitor is ICA-1 which is specific for PKC-ι. An example of a pan-aPKC inhibitor is 2-acetyl-1,3-cyclopentanedione (ACPD), which inhibits both PKC-ζ and PKC-ι, but not PKC-α, PKC-β, PKC-δ, or PKC-ε.

A method of inhibiting ovarian tumor cell proliferation is presented comprising contacting the tumor cells with a therapeutically effective amount of a protein kinase C (PKC) inhibitor. The PKC inhibitor may inhibit at least one atypical protein kinase (aPKC) selected from the group consisting of PKC-ι, PKC-ζ, or combinations thereof. In some embodiments, the PKC inhibitor is specific to a single aPKC while in other embodiments the PKC inhibitor is a pan-aPKC inhibitor which is effective against different isoforms of PKC. An example of a PKC-specific inhibitor is ICA-1 which is specific for PKC-ι. An example of a pan-aPKC inhibitor is 2-acetyl-1,3-cyclopentanedione (ACPD), which inhibits both PKC-ζ and PKC-ι, but not PKC-α, PKC-β, PKC-δ, or PKC-ε.

A method of reducing levels of at least one atypical PKC (aPKC) in ovarian tumor cells is also presented comprising contacting the tumor cells with a therapeutically effective amount of a PKC inhibitor. The aPKC may be PKC-ι, PKC-ζ, or combinations thereof. The PKC inhibitor may be a pan-aPKC inhibitor or specific to a single aPKC. For example, the PKC inhibitor may be ICA-1 and ACPD.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
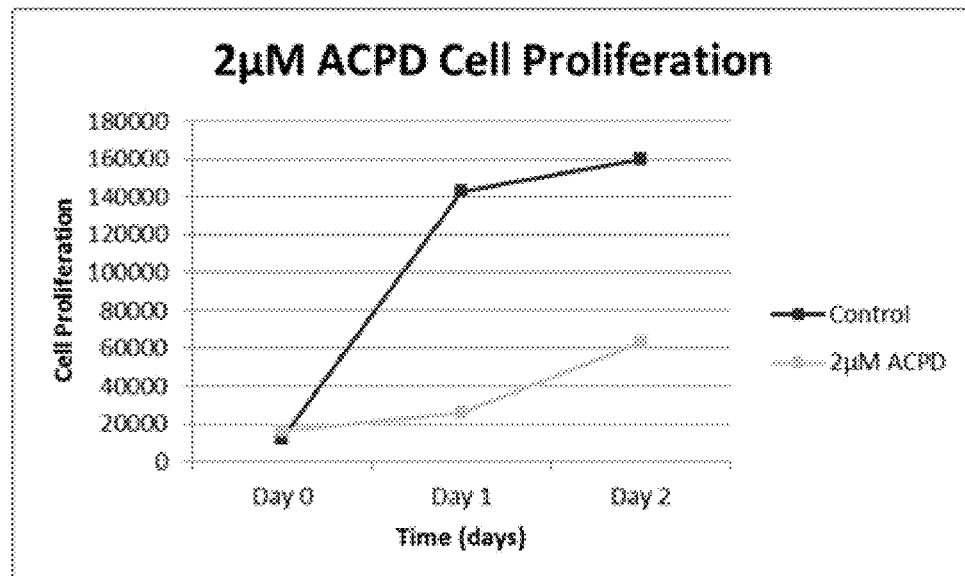
FIG. 1 is a graph depicting the effects of ACPD on HEY ovarian cancer cell proliferation. As shown in the graph, administering 2 μM ACPD to ovarian cancer cells reduced cell proliferation by 81.75% at 24 hours and 60.5% at 48 hours.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

DEFINITIONS

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise.

The term "cell" or "cells" is used synonymously herein and refers to in vitro cultures of mammalian cells grown and maintained as known in the art, as well as biological samples obtained from tumor specimens or normal specimens in vivo.

The term "agent" as used herein describes a composition, compound, chemical or extract that can be administered or tested by the present invention as a modulator of a PKC. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof "Agent" is used interchangeably herein with "compound", "composition", "chemical", "drug", and "extract".

The term "PKC inhibitor" as used herein refers to an agent that inhibits the activity or reduces/inhibits the expression of one or more isoforms of protein kinase C (PKC). Examples of such inhibitors include, but are not limited to, ICA-1, ACPD, fludarabine and derivatives thereof; aurothioglucose (1); aurothiomaleate (2); auranofin (3); thimerosal; phenylmercuric acetate; ebselen; cisplatin; taxol; apomorphine; pyrantel pamoate; gossypolacetic acid complex; ellagic acid; hexestrol; Pachastrissamine and its stereoisomers (6-10); ZIP (11); allosteric inhibitors (12-14) which bind the PIF-1 site and regulate activity through the C1 domain; a series of phenylthiopenes (15-17); a compound containing a maleimide substructure (19); speciosterosulfates (sterolsulfates) (20-23); a series of compounds having an indazole-benzimidazole motif (24-25); a series of ATP-competitive thieno[2, 3-d]pyrimidine analogues (26-27); a pyrrole amide PKCzI257.3 (28); and a series of 3-hydroxy-2-(3-hydroxyphenyl)-4H-1-benzopyran-4-ones which may bind to the ATP-cleft of the kinase through a keto-hydroxyl motif in multiple conformations (30-33); and derivatives thereof. Bolded numbers in parentheses refer to the corresponding numbered structure of the agent listed in the Background section of the application.

The term "pan-aPKC inhibitor" as used herein refers to an agent that inhibits the activity or reduces/inhibits the expression of at least one atypical PKC such as PKC-ι or PKC-ζ. Examples of such agents include, but are not limited to ACPD, pachastrissamine and its stereoisomers, and derivatives thereof.

The terms "PKC-ι inhibitor" as used herein refers to an agent that inhibits PKC-ι activity or reduces or inhibits expression of PKC-ι. The agent may be specific to PKC-ι or alternatively may be a pan-aPKC inhibitor that is effective against different aPKC isoforms, such as ACPD. The inhibitor can be a polypeptide that binds to a unique sequence in the catalytic domain of PKC-ι and inhibits its activity; a polypeptide that is involved with the interaction of PKC-ι with other signaling molecules; a polypeptide having sequence homology to a specific region of a signaling molecule that mediates the binding of these molecules to PKC-ι; or a small molecule inhibitor, such as ICA-1 and derivatives thereof.

The terms "PKC-ζ inhibitor" as used herein refers to an agent that inhibits PKC-ζ activity or reduces or inhibits expression of PKC-ζ. The agent may be specific to PKC-ζ or alternatively may be a pan-aPKC inhibitor that is effective against different aPKC isoforms, such as ACPD. The inhibitor can be a polypeptide that binds to a unique sequence in the catalytic domain of PKC-ζ and inhibits its activity; a polypeptide that is involved with the interaction of PKC-ζ with other signaling molecules; a polypeptide having sequence homology to a specific region of a signaling molecule that mediates the binding of these molecules to PKC-ζ; or a small molecule inhibitor. Examples of a PKC-ζ inhibitor include, but are not limited to, ZIP, ACPD, speciosterosulfates (sterolsulfates), and derivatives thereof.

"Subject" is used to describe an animal, preferably a human, to whom treatment is administered, including prophylactic treatment with the compositions of the present invention. "Subject" and "patient" are used interchangeably herein.

The term "treatment" or "treating" as used herein refers to the ability to ameliorate, suppress, mitigate, or eliminate the clinical symptoms after the onset of a disease state. Treatment can include chemicals, such as chemotherapeutic agents or test compounds, and/or non-chemical treatment such as radiation, electrical pulses, and magnetic fields that may be used with any of the agents disclosed herein. An effective or successful treatment provides a clinically observable improvement.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

"Administration" or "administering" is used to describe the process in which the PKC inhibitors of the present invention are delivered to a patient for treatment purposes. This includes parental, referring to parenterally (intramuscularly, intraperitoneally, intraarterially, intravenously, subcutaneously), orally, topically, transdermally, or vaginally and other routes that allow the PKC inhibitor to contact tumor cells. The PKC inhibitor may be administered independently or in combination with other compounds, such as other chemotherapeutic compounds.

A "therapeutically effective amount" as used herein is defined as concentrations or amounts of components which are sufficient to effect beneficial or desired clinical results, including, but not limited to, inhibiting neoplastic transformation of cells; inhibiting inappropriate cell growth; inhibiting the proliferation of neoplastic/cancerous cells; inducing apoptosis in neoplastic/cancerous cells; decreasing the level of PKC-ι or PKC-ζ in a sample; and enhancing the therapeutic effect of chemotherapy medications. Compositions of the present invention can be used to effect a favorable change in the condition whether that change is an improvement or a complete elimination of symptoms due to neoplasia/cancer. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing cancer treatment or enhancing cancer treatment without causing significant side effects or adverse reactions. For the specific PKC-ι inhibitor ICA-1, the therapeutically effective concentration was found to be between about 800 nM to about 10 μM. In some embodiments the range is between about 1 μM to about 2 μM. In some embodiments, the therapeutically effective concentration is about 2 μM. For ACPD, the therapeutically effective concentration was found to be between about 800 nM to about 10 μM. In some embodiments, the therapeutically effective concentration was found to be about 2 μM. Therapeutically effective concentrations for other PKC-ι inhibitors can be readily determined by those of ordinary skill in the art.

The term "neoplasia", "cancer", "tumor", "cancerous", and malignant" as used herein, refer to the physiological condition in mammals that is typically characterized by unregulated cell growth or the presence of tumors. Examples of cancer benefited by the present invention include, but are not limited to, ovarian cancer, breast cancer, prostate cancer and glioblastoma.

The inventors examined the in-vitro efficacy of the pan-atypical PKC inhibitor, 2-acetyl-1,3-cyclopentanedione (ACPD; *Diabetes*. 2014 Apr. 4) and the novel PKC-iota inhibitor, ICA-1, ([4-(5-amino-4-carbamoylimidazol-1-yl)-2,3-dihydroxycyclopentyl]methyl dihydrogen phosphate) [*The Inter. J. Biochem. & Cell Biol.* 43:784-794 (2011)] on HEY ovarian cancer cell proliferation and RNA concentration. In contrast to ACPD which inhibits both PKC-iota (PKC-ι) and PKC-zeta (PKC-ζ), ICA-1 specifically inhibits the activity of PKC-ι but not PKC-ζ.

PKC-ι and PKC-ζ are 84% homologous with respect to the amino acid sequences of their catalytic domain (Pillai, P et al (2011) A novel PKC-ι inhibitor abrogates cell proliferation and induces apoptosis in neuroblastoma. Int J Biochem Cell Biol, 43:784-94). PKC-ι and PKC-ζ have been shown in many studies to play a role in the invasive potential and drug-induced resistance of cancer cells but few inhibitors against these novel protein kinases have been developed.

PKC-ι has been shown to play an important role in the invasiveness of breast cancer cells through the up-regulation and co-localization of membrane type 1-matrix metalloproteinase (Rosse, C, et al (2014) Control of MT1-MMP transport by atypical PKC during breast-cancer progression. Proc Natl Acad Sci USA, 111 (18):E1872-9).

PKC-ι has also been shown to promote Hedgehog ligand production and lung squamous cell growth through the SOX2 transcription factor which provides evidence that targeting PKC-ι may be the key in treating Hedgehog dependent cancers (Atwood, S X et al (2014) "Atypical" regulation of Hedgehog-dependent cancers. Cancer Cell, 25(2):133-4). It has previously been shown that the hedgehog pathway is involved in the development and progression of ovarian cancer. (Chen, Q. et al., Hedgehog signaling pathway and ovarian cancer, *Chinese Journal of Cancer Research,* 2013, 25(3): 346-53).

Many studies have shown the importance of PKC-ι in promoting cancer cell growth and resistance but few have introduced PKC-ι inhibitors. ICA-1 has been shown to specifically inhibit PKC-ι which may provide a more targeted and effective treatment against cancers.

PKC-ζ has been shown to regulate survivin expression levels and inhibits apoptosis in colon cancer cells. (Umemori, Y et al (2014) PKC-ζ regulates survivin expression and inhibits apoptosis in colon cancer. Intl J Oncol). Survivin levels in ovarian cancer have been correlated with the progression of the disease (Liguang et al., 2007). It has been previously shown that PKC-ζ has a pro-apoptotic function in ovarian cancer (Nazarank et al., 2010).

It was found that both PKC-ι and PKC-ζ are implicated in ovarian cancer. The pan-aPKC inhibitor ACPD was shown herein to inhibit both PKC-ι and PKC-ζ.

Results

Figure 2:
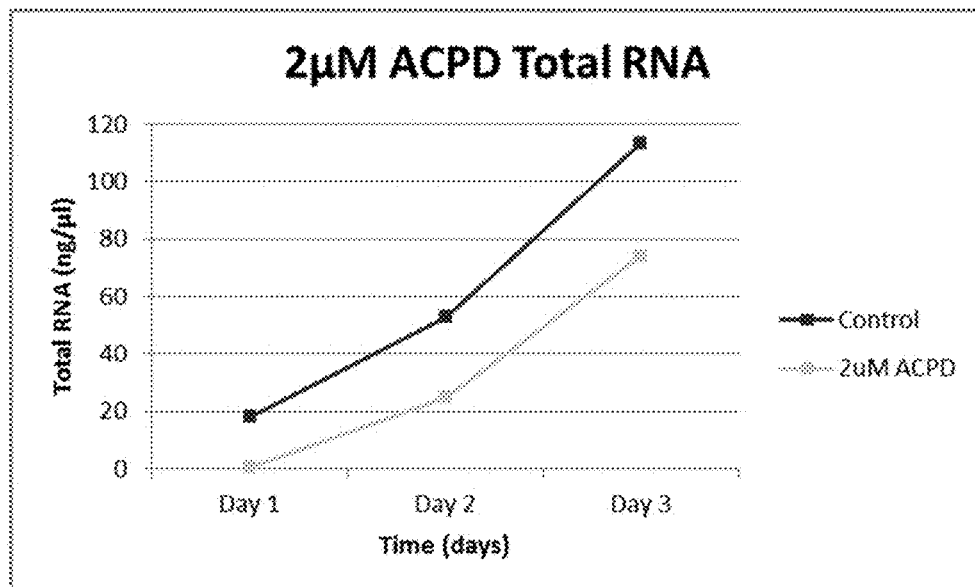
FIG. 2 is a graph depicting the effects of ACPD on HEY ovarian cancer cell RNA levels. As shown in the graph, administration of 2 µM ACPD to ovarian cancer cells reduced total RNA by 97.4% at 24 hours; 52.4% at 48 hours and 34.3% at 72 hours.

Results showed that incubation of HEY ovarian cancer cells with ACPD (2 μM) inhibited proliferation by 82% compared to controls and RNA levels were reduced by 97% at 24 hours post-treatment (FIGS. 1 and 2). A 60% reduction in cell proliferation was observed after 48 hours. (FIG. 1) RNA levels were shown to be reduced 52% at 48 hours and 34% at 72 hours. (FIG. 2)

Given that the reduction in tumor cell proliferation and RNA levels is more pronounced at 24 hours after treatment as opposed to 48 hours after treatment, it seems as if the effectiveness of the treatment decreases with time. The reduction may decrease after 48 hours due to resistance that the cells may be developing. In order to overcome this resistance, treatment may need to be given more frequently and the dosage may need to be increased every day.

With regard to the decrease in RNA levels, it seems as if the reduction is lessened by about half for each day after treatment. These results have implications for both dose as well as treatment schedule. The dosage of the treatment may need to be increased each day in order to overcome any kind of resistance the cells may be developing. Treatments may need to be given more than once every 24 hours; the increase in the number of treatments per day may mitigate some of the reduction in the effectiveness.

Incubation of HEY ovarian cancer cells with ICA-1 (2 μM) for 72 hours showed a 12% reduction in cell proliferation at 72 hours. (FIG. 3) A 16% reduction in RNA levels was shown at 72 hours. (FIG. 4)

Figure 3:
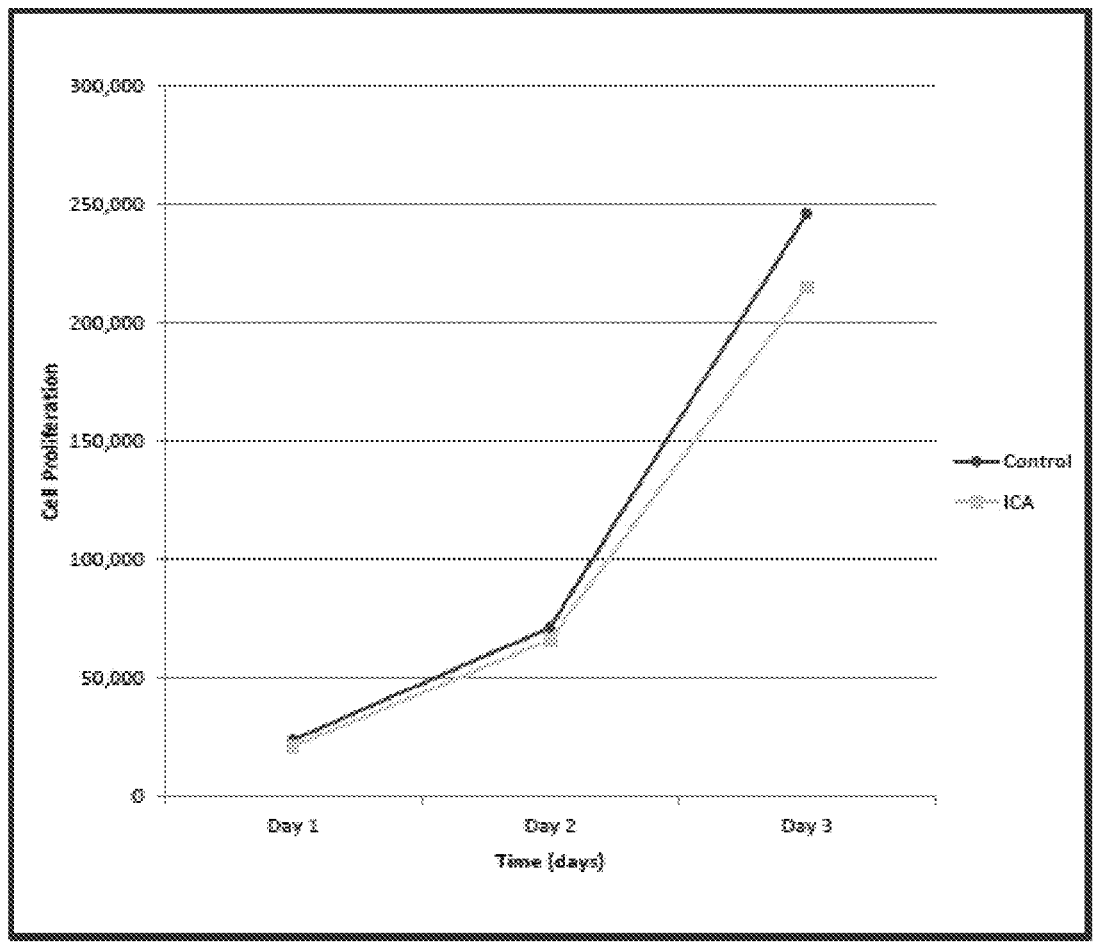
FIG. 3 is a graph depicting the effects of ICA-1 on HEY ovarian cancer cell proliferation. HEY ovarian cancer cells were treated with 2 µM ICA-1 for 72 hours and cell proliferation was measured using a Trypan blue exclusion assay. It was found that ICA-1 reduced cell proliferation by 12% at 72 hours.
Figure 4:
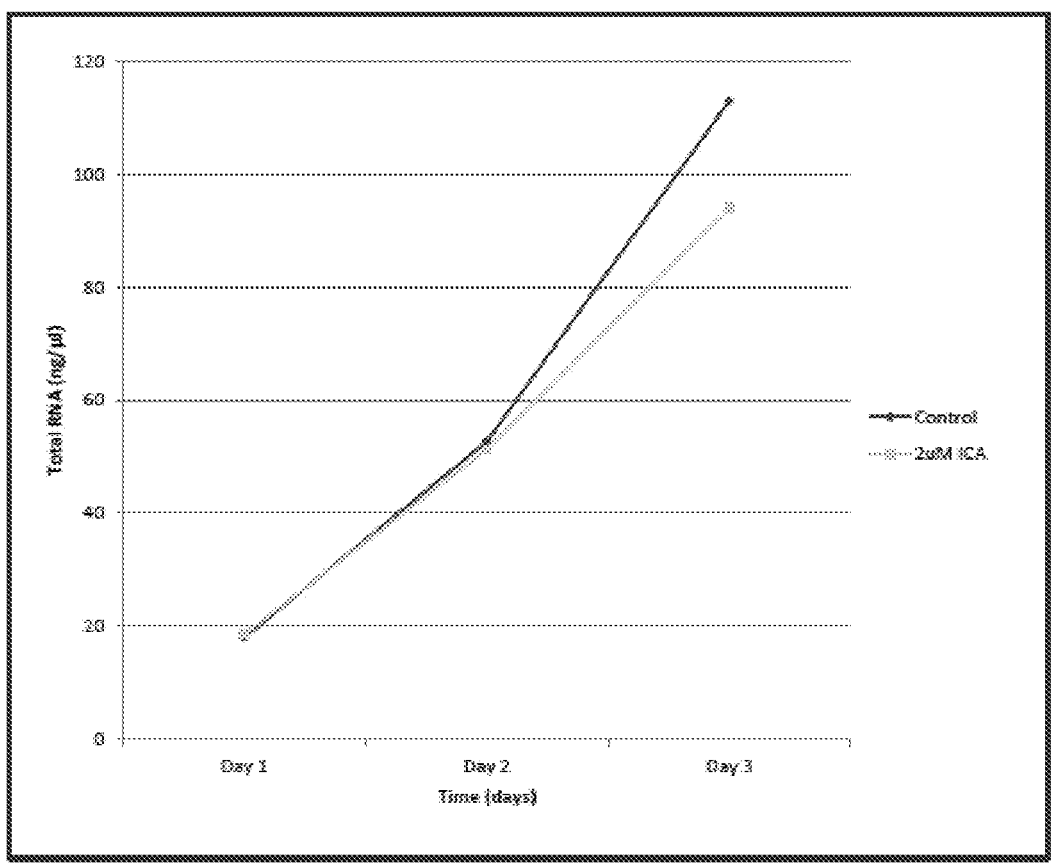
FIG. 4 is a graph depicting the effects of ICA-1 on HEY ovarian cancer cell RNA levels. HEY ovarian cancer cells were treated with 2 µM ICA-1 for 72 hours and the RNA was measured using NanoDrop1000 Spectrophotometer. It was found that ICA-1 reduced total RNA by 16% at 72 hours.

As shown in FIGS. 3 and 4, treatment with ICA-1 had little effect on cell proliferation or RNA levels at 24 and 48 hours after treatment which indicates a longer incubation period with the cells is needed before a noticeable reduction in cell proliferation occurs.

Although ACPD and ICA-1 both inhibit cell proliferation in HEY ovarian cancer cells, ACPD is over five times more effective than ICA-1. Several scenarios are possible to account for this difference. For example, this result can be due to both PKC-ι and PKC-ζ being implicated in ovarian cancer. Different pathways could be getting activated that are causing a different response with the two drugs. ACPD may be more effective earlier because it is targeting multiple PKC's while ICA-1 is more specific. In addition, certain ovarian cancer cells lines may respond differently to treatment with ICA-1 and ACPD. ACPD and ICA-1 were also shown to decrease the total RNA concentration in HEY ovarian cancer cells. (FIGS. 1-4) ACPD inhibits both PKC-ι and PKC-ζ while ICA-1 only inhibits PKC-ι. These results indicate that PKC-zeta also plays a role in cell proliferation and regulating RNA synthesis, structure, or activity.

Given that both ACPD and ICA-1 reduce the proliferation of ovarian cancer cells and reduce the levels of RNA in cells, PKC inhibitors have implications to increase the overall prognosis of patients having ovarian cancer.

Figure 5:
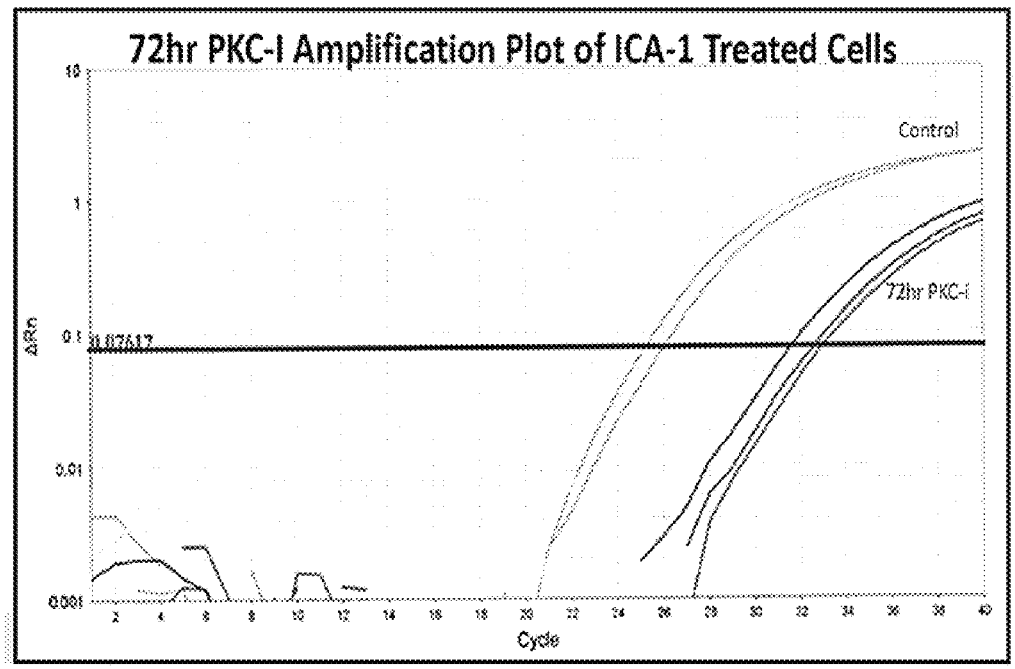
FIG. 5 is an image depicting a 72-hour PKC-I amplification plot of ICA-1 treated cells. qRT-PCR was performed on 2 µM ICA-1 treated HEY cells. ICA-1 was found to inhibit the PKC-I gene more than PKC-Z. There was no effect on interferon gamma or HPRT-1 (housekeeping gene).

As shown by qRT-PCR, ICA-1 more specifically inhibits PKC-ι than PKC-ζ. (FIG. 5) This result confirms that ICA-1 is a PKC-ι specific inhibitor.

Figure 6:
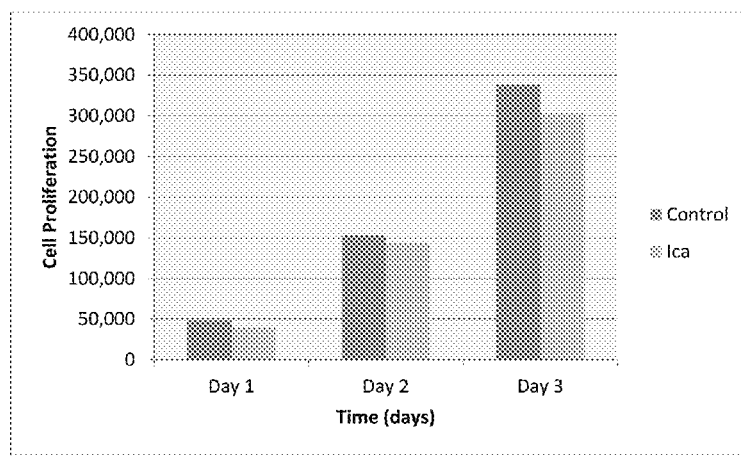
FIG. 6 is a graph depicting the effects of 400 nM ICA-1 on HEY Cell Proliferation. A 10% reduction was seen in cell proliferation following a 72 hour treatment of HEY ovarian cancer cells with 400 nM ICA-1.
Figure 8:
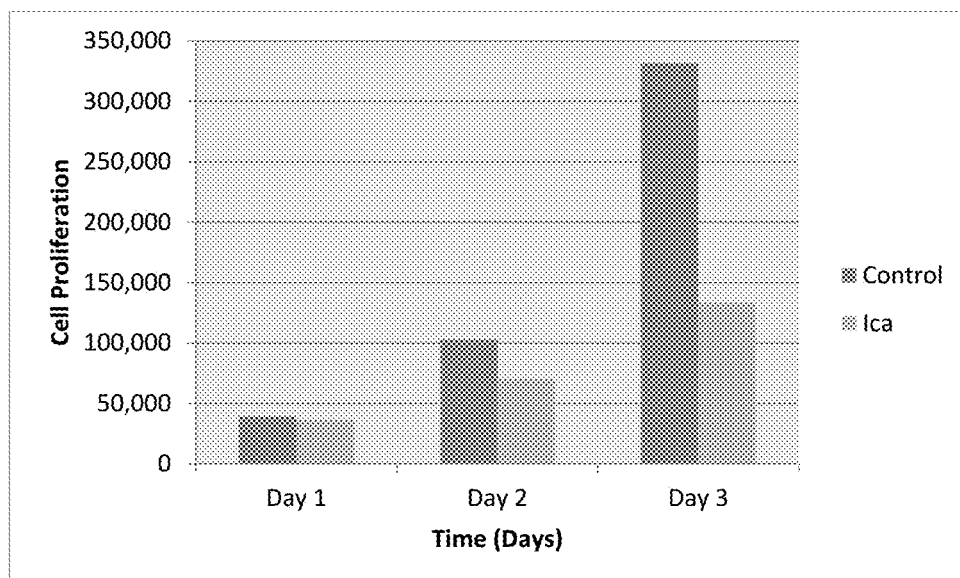
FIG. 8 is a graph depicting the effects of 800 nM ICA-1 on HEY Cell Proliferation. A 60% reduction was seen in cell proliferation following a 72 hour treatment of HEY ovarian cancer cells with 800 nM ICA-1.

As depicted in FIG. 6, a 10% reduction was seen in cell proliferation following a 72 hour treatment of HEY ovarian cancer cells with 400 nM ICA-1. A 60% reduction was seen in cell proliferation following a 72 hour treatment of HEY ovarian cancer cells with 800 nM ICA-1. (FIG. 8)

Figure 7:
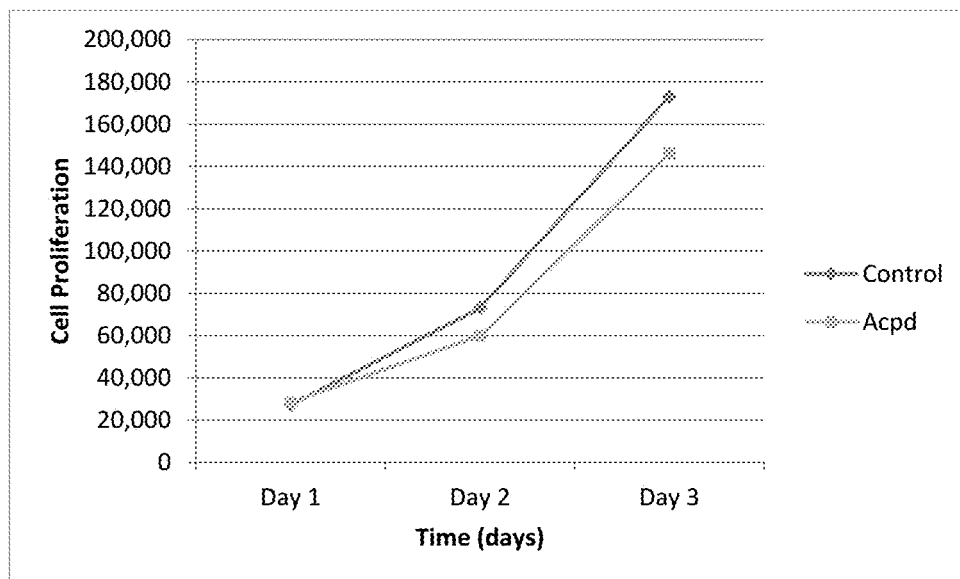
FIG. 7 is a graph depicting the effects of 800 nM ACPD on HEY Cell Proliferation. A 16% reduction was seen in cell proliferation following a 72 hour treatment of HEY ovarian cancer cells with 800 nM ACPD.
Figure 9:
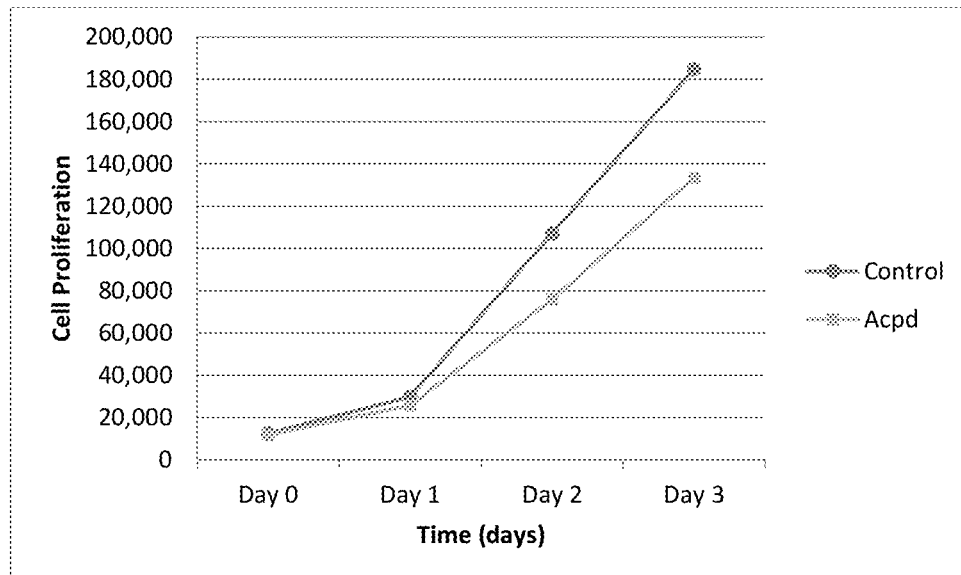
FIG. 9 is a graph depicting the effects of 1.8 µM ACPD on HEY Cell Proliferation. A 28% reduction was seen in cell proliferation following a 72 hour treatment of HEY ovarian cancer cells with 1.8 µM ACPD.

A 16% reduction was seen in cell proliferation following a 72 hour treatment of HEY ovarian cancer cells with 800 nM ACPD. (FIG. 7) A 28% reduction was seen in cell proliferation following a 72 hour treatment of HEY ovarian cancer cells with 1.8 μM ACPD. (FIG. 9)

Figure 10:
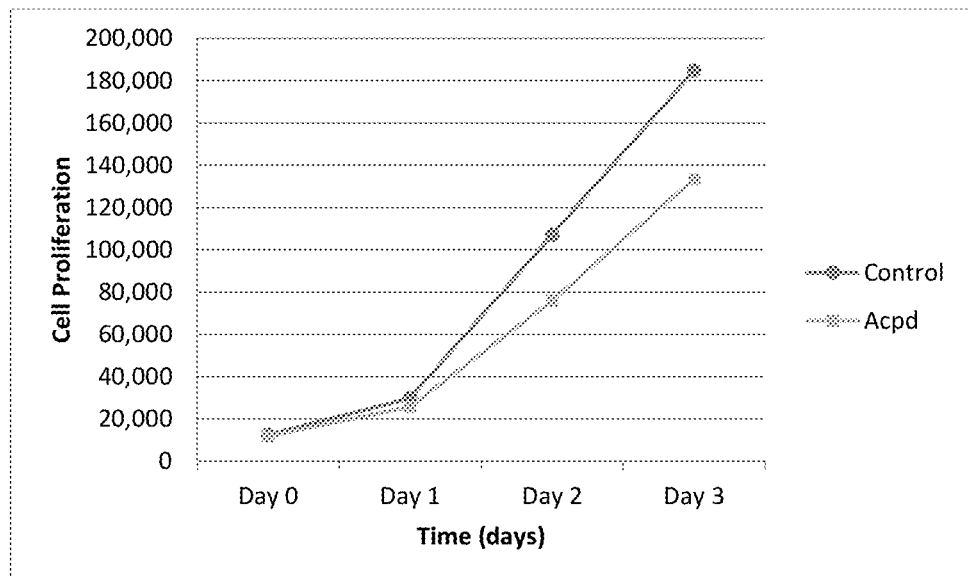
FIG. 10 is a graph depicting HEY Cell Total RNA Concentration following treatment with 1.8 µM ACPD. A 38% reduction was seen in total RNA concentration following a 72 hour treatment of HEY ovarian cancer cells with 1.8 µM ACPD.

A 38% reduction was seen in total RNA concentration following a 72 hour treatment of HEY ovarian cancer cells with 1.8 μM ACPD. (FIG. 10)

FIGS. 6-10 show the dose-response relationship between ovarian cancer cells and treatment with either ICA-1 or ACPD. The dose-response relationship is used to provide information regarding the optimal concentration and toxicity of treatment. As shown in the figures, the optimal range of concentrations for both ICA-1 and ACPD was between about 800 nM to 10 μM. Exceeding 10 μM resulted in possible toxicity.

The inventors have shown that HEY ovarian cancer cells are affected by treatment with ICA-1 and ACPD at concentrations as low as 800 nM to as high as 10 μM. The treatment affects the proliferation of the cancer cells by reducing it. The reduction in proliferation varies at different concentrations and depends upon which drug is being used. The exact mechanism of action of the drugs has yet to be determined but the inventors have shown the effectiveness of the drugs. Administration of the drugs can improve the overall survival of a patient with ovarian cancer as well as assist in overcoming chemotherapeutic resistance built up by the cells.

The reduction in RNA levels provide further evidence of the reduction in proliferation. A decrease in RNA levels points to the fact that there are less cells. The qPCR plot shows that there is a lower amount of PKC-ι in the cells as compared to the controls which means that treatment with ICA-1 is indeed inhibiting PKC-ι, as expected. The PKC-ι in the cells treated with ICA-1 for 72 hours is amplifying at a later cycle than the control cells which indicates there is a lower amount of PKC-ι in the treated cells.

Taking the results from the cell proliferation experiments, the RNA levels experiments and the qPCR experiment into account, it was found that not only do the PKC inhibitors decrease cell proliferation, they also decrease the levels of PKC-ι and PKC-ζ in cells. Given the results shown herein, PKC inhibitors, in particular atypical PKC inhibitors, may be used as potential therapies for treating ovarian cancer by reducing tumor cell proliferation as well as reducing the levels of PKC-ι and PKC-ζ in the cell. The use of PKC inhibitors could improve the overall survival prognosis of patients having ovarian cancer. These results suggest the potential of ACPD and ICA-1 as chemotherapeutic agents.

While the studies were conducted in vitro, the results are applicable to in vivo use. The in vitro studies allow the effects of various PKC inhibitors to be seen on ovarian cancer cells that were extracted from patients. These in vitro results provide evidence of the efficacy of a given inhibitor against cancer cells. These cancer cells may then be implanted into an animal model, such as mouse, and the PKC inhibitor administered to the animal to study the in vivo effects of the drug. The in vivo studies allow for the determination of the effects of the inhibitors not only on the cancer cells themselves but also on the rest of the body of the patient.

Materials and Methods

Materials 2-acetyl-1,3-cyclopentanedione (ACPD) was purchased from Sigma-Aldrich (St. Louis, Mo.). It was dissolved in sterile distilled water before use.

ICA-1 was purchase from United Chem Resources in Alabama. ICA-1 was weighed and dissolved in water to create a 100 mM stock solution. From this solution, serial dilutions were done to create a 1 mM stock solution which was then used for treatment.

Dulbecco's phosphate buffered saline without Mg2+ and Ca2+(DPBS) was purchased from the American Type Culture Collection (Rockville, Md.). Trypsin-EDTA (ethylenediaminetetraacetic acid) solution was purchased from Life Technologies (Carlsbad, Calif.). The Rneasy Mini Kit was purchased from Qiagen. PCK-iota antibody was purchased from Santa Cruz Biotechnology, Inc. (Dallas, Tex.).

Cell Culture

HEY human ovarian carcinoma cells were obtained from Dr. Meera Nanjundan's laboratory at the University of South Florida. The cells were grown as a monolayer in a T25 tissue culture flask with 5 mL of growth medium and maintained in a 37° C. incubator with 5% $CO_2$. The RPMI1640 growth medium was obtained from and American Type Culture Collection (ATCC) and Life Technologies (Carlsbad, Calif.). The medium was supplemented with 10% fetal bovine serum (FBS) and a mix of the antibiotics Penicillin (10,000 IU) and Streptomycin (10,000 μg/ml) in a 100× concentration which was purchased from Corning.

Cell Viability Assay

HEY cells were cultured in a T25 cell culture flask. 13,000 cells were seeded into each well in a 6-well culture plate. ACPD was weighed and dissolved in water to create a 100 mM stock solution. From this solution, serial dilutions were done to create a 1 mM stock solution which was then used for treatment. In order to assess the effect of ACPD on cell viability, three wells were treated with 2 μM ACPD while the other three wells were left untreated as controls. The treatment period was 72 hours with the growth medium being changed every 24 hours. The cells were also washed with DPBS every time the growth medium was changed. Cell viability was determined at 24, 48 and 72 hours using a Trypan blue exclusion assay where 30 μL of the cell suspension was added to 30 μL of Trypan blue. The number of unstained cells was counted using a hematocytometer. The same procedures were used for ICA-1.

RNA Isolation and Estimation

RNA was isolated from the treated and untreated cells using the Rneasy Mini Kit and protocol. The total RNA concentration was estimated using the NanoDrop1000 spectrophotometer.

Western Blot Analysis

The experiments were performed as per the protocol described by Patel et al. (2008), herein incorporated by reference. Briefly, cells were cultured in T75 flasks in monolayers. For treatment, 40,000 cells were seeded into T75 flasks and treated for 72 hours with ICA-1 and ACPD. The proliferation was measured each day by a Trypan Blue exclusion assay which involved staining the cells with Trypan Blue and counting them under a microscope using a hemocytometer.

Real-Time Polymerase Chain Reaction (qRT-PCR)

qRT-PCR was performed using the Applied Biosystems ViiA7 Real-Time PCR system. qRT-PCR was done on three genes (PKC-iota, PKC-zeta, IFN-g) in addition to the housekeeping gene (HPRT-1).

CONCLUSION

Results showed that incubation of HEY ovarian cancer cells with ICA-1 (1 μM) decreased proliferation by 41% compared to controls at 72 hours post-treatment. ICA-1 (2 μM) reduced RNA levels by 17% at 72 hours post-treatment compared to controls. In contrast, ACPD (2 μM) inhibited proliferation by 82% compared to controls and RNA levels were reduced by 97% at 24 hours post-treatment. These results suggest the potential of ICA-1 and ACPD as chemotherapeutic agents.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of treating ovarian cancer in a patient in need thereof comprising inhibiting at least one atypical protein kinases (aPKC) selected from the group consisting of PKC-iota, PKC-zeta, or combinations thereof by administering to the patient in need thereof a therapeutically effective amount of a protein kinase C (PKC) wherein the PKC inhibitor is selected from the group consisting of 2-acetyl-1,3-cyclopentanedione (ACPD) and ICA-1.

2. The method of claim 1, wherein the therapeutically effective amount of the PKC inhibitor is a concentration between about 800 nM to about 10 μM.

3. The method of claim 1, wherein the PKC inhibitor is specific to a single aPKC.

4. The method of claim 3, wherein the aPKC is PKC-iota.

5. The method of claim 4, wherein the PKC inhibitor is ICA-1.

6. The method of claim 1, wherein the PKC inhibitor is 2-acetyl-1,3-cyclopentanedione (ACPD).

7. A method of inhibiting ovarian tumor cell proliferation comprising inhibiting at least one atypical protein kinases (aPKC) selected from the group consisting of PKC-iota, PKC-zeta, or combinations thereof by contacting the tumor cells with a therapeutically effective amount of a protein kinase C (PKC) inhibitor wherein the PKC inhibitor is selected from the group consisting of 2-acetyl-1,3-cyclopentanedione (ACPD) and ICA-1.

8. The method of claim 7, wherein the therapeutically effective amount of the PKC inhibitor is a concentration between about 800 nM to about 10 µM.

9. The method of claim 7, wherein the PKC inhibitor is specific to a single aPKC.

10. The method of claim 9, wherein the aPKC is PKC-iota.

11. The method of claim 10, wherein the PKC inhibitor is ICA-1.

12. The method of claim 7, wherein the PKC inhibitor is 2-acetyl-1,3-cyclopentanedione (ACPD).

* * * * *